United States Patent [19]

Pedersen

[11] Patent Number: 4,491,730
[45] Date of Patent: Jan. 1, 1985

[54] METHOD AND APPARATUS FOR FEEDBACK STABILIZED PHOTOMETRIC DETECTION IN FLUIDS

[75] Inventor: Norman E. Pedersen, Wilmington, Mass.

[73] Assignee: Panametrics, Inc., Waltham, Mass.

[21] Appl. No.: 312,936

[22] Filed: Oct. 19, 1981

Related U.S. Application Data

[63] Continuation-in-part of Ser. No. 178,190, Aug. 14, 1980.

[51] Int. Cl.³ .............................................. G01J 1/00
[52] U.S. Cl. .................................. 250/343; 250/345; 356/433
[58] Field of Search ............ 250/343, 345, 373, 461.1, 250/252.1; 356/433, 436

[56] References Cited

U.S. PATENT DOCUMENTS

| | | | |
|---|---|---|---|
| 3,897,154 | 7/1975 | Hawes | 250/345 X |
| 4,057,734 | 11/1977 | Barringer | 250/345 X |
| 4,176,963 | 12/1979 | Fabinski et al. | 250/345 X |

*Primary Examiner*—Janice A. Howell
*Attorney, Agent, or Firm*—Lahive & Cockfield

[57] ABSTRACT

A photometric detection method and apparatus employ a variable beam modulation device, such as a planar oscillating disk whose reflectance and transmittance with respect an incident beam of electromagnetic radiation vary with disk angular position, to form, from an incident beam of radiation, two amplitude modulated correlated component beams. Preferably the amplitudes of the component beams vary sinusoidally, 180° out of phase. In one illustrative embodiment, one of the component beams passes through a sample fluid, which absorbs a portion of the radiation at a wavelength characteristic of a selected component. The second component beam passes through a reference path and provides a reference signal relative to which changes in the sample fluid are measured. A feedback mechanism is provided to automatically adjust for variations which can occur while the apparatus is operating. The component beams are combined and are directed onto a detector which produces an output proportional to the intensity of the combined beam. By properly selecting the parameters of the system, the AC component of the combined signal, if any, provides a sensitive measure of the presence generally and if calibrated the relative density, of the selected sample fluid.

30 Claims, 9 Drawing Figures

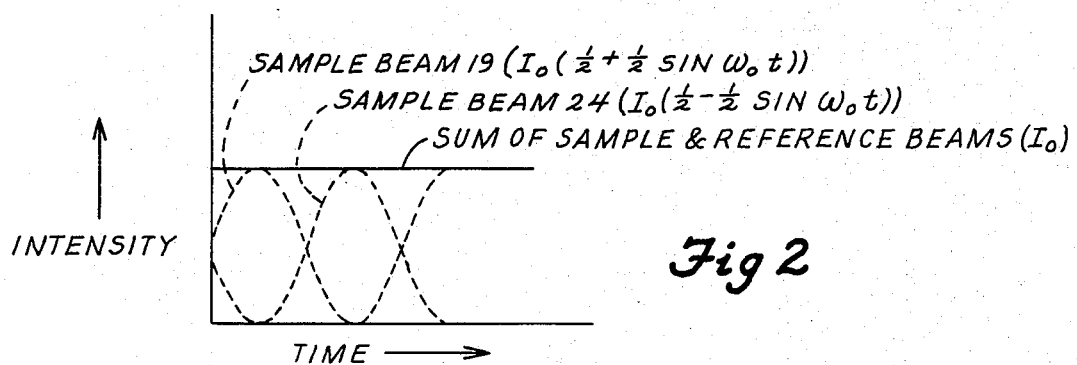
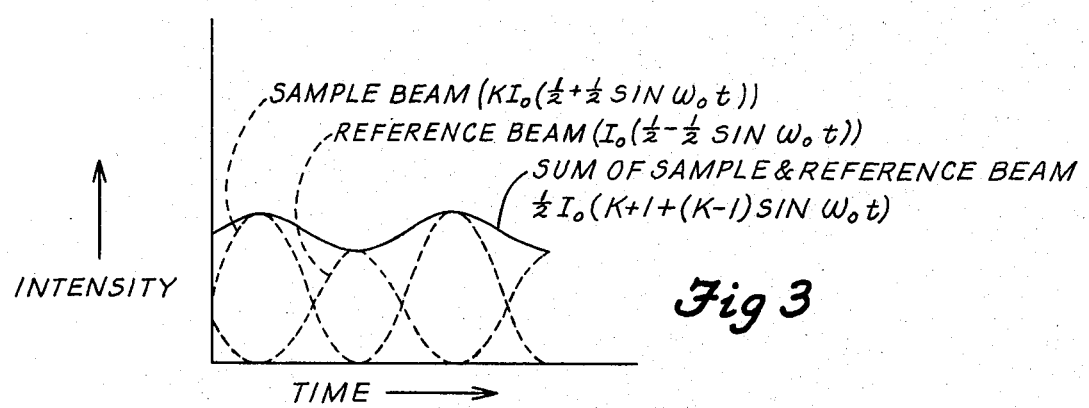

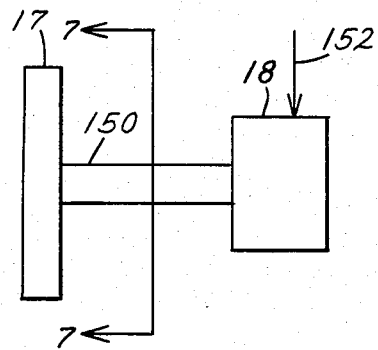
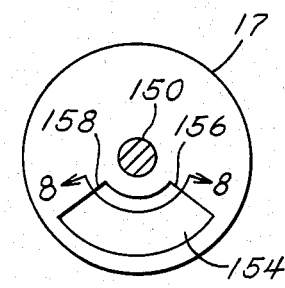
Fig 6  Fig 7
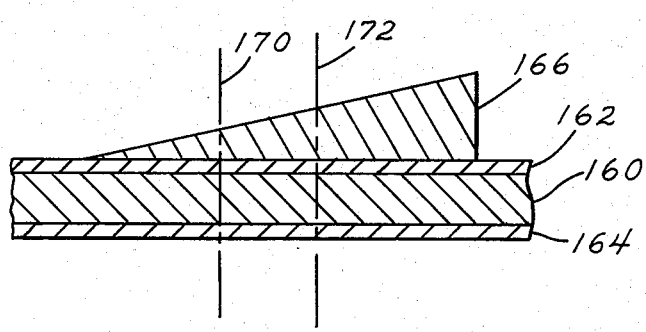
Fig 8

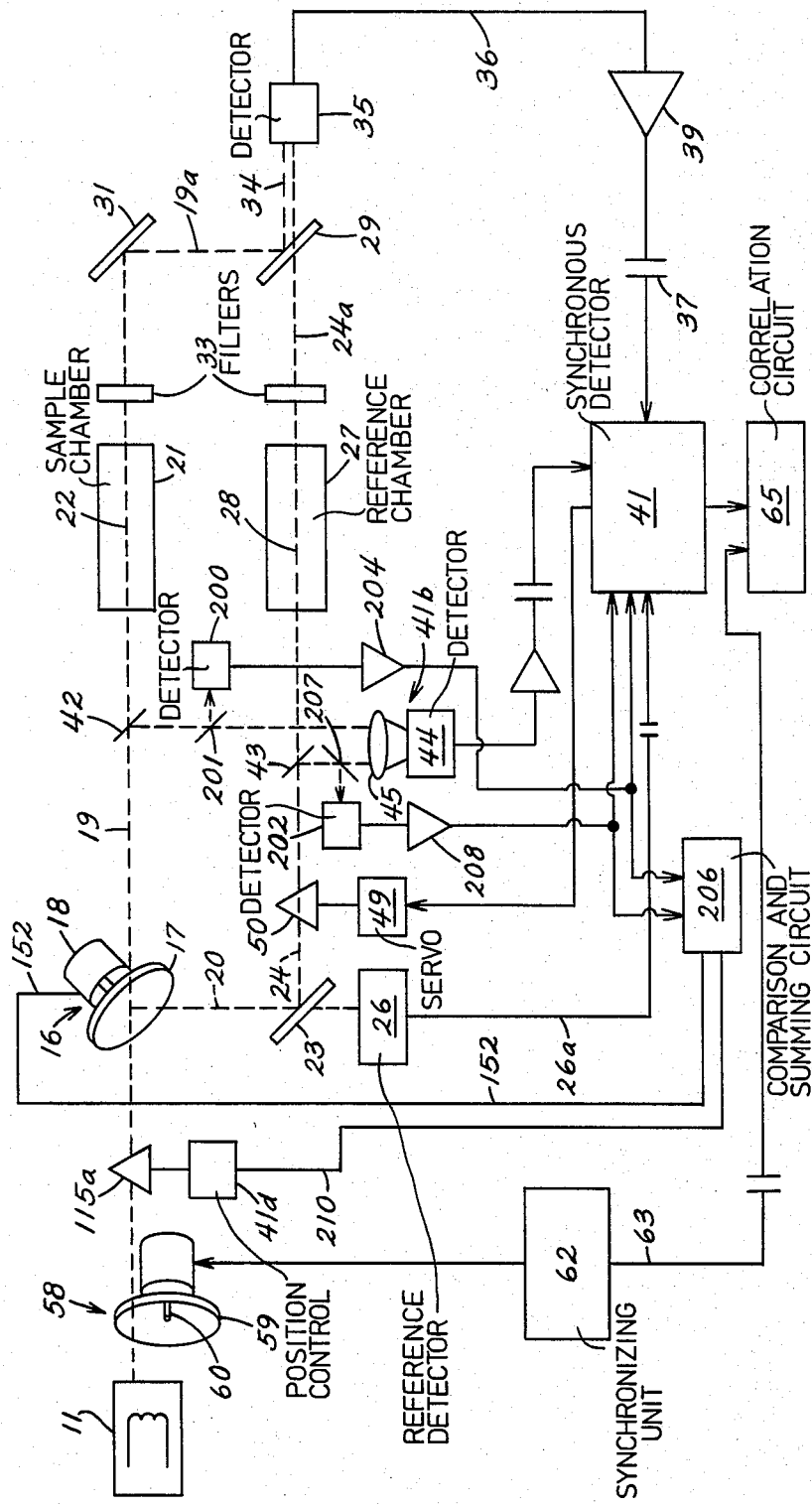

METHOD AND APPARATUS FOR FEEDBACK STABILIZED PHOTOMETRIC DETECTION IN FLUIDS

CROSS-REFERENCE TO RELATED APPLICATION

This application is a continuation-in-part of my co-pending application U.S. Ser. No. 178,190, filed Aug. 14, 1980, and titled Method and Apparatus for Photometric Detection in Fluids.

BACKGROUND OF THE INVENTION

The present invention relates generally to the field of photometric detection and analysis, and more particularly to apparatus and methods for detecting and/or measuring the energy absorption by a fluid medium in a sample chamber.

In the qualitative and quantitative analysis of fluids, a well known analysis technique calls for a beam of electromagnetic radiation, such as visible light or infrared radiation, to be time-chopped (on-off modulated) to form a sample and a reference beam. The sample beam is directed through a sample of a fluid medium being examined; and selected components within the medium, if present, attentuate the energy of the incident beam at particular wavelengths characteristic of the selected fluid components. By measuring the amplitude of the sample beam, relative to the reference beam, after it passes through the fluid (making the measurement at one or more wavelengths), it is possible to both detect and identify the selected fluid components and determine the density thereof.

Generally, however, these photometric analysis measurement techniques attempt to measure small changes of signal which "ride" on a relatively large quiescent or base signal. Thus, changes of for example 0.1% or less in the overall signal are not unusual in order to accurately determine the quantity of selected fluids in the sample chamber. These small signal amplitude changes occur because the amount of energy absorption at a wavelength of interest is relatively small compared to the magnitude of the incident and measured signals. Therefore, in order to make these measurements extremely precise, low noise, complex measurement techniques are generally employed.

As a result, at least one known apparatus configuration mechanically modulates, by successively blocking and unblocking, a reference and a sample beam respectively, for providing two correlated modulated waveform beams having a 180° out of phase AC component. These two beams, if not attenuated or if attenuated by the same amounts, can be combined to provide a single measurement signal having a constant amplitude. If however the beams are attenuated by different amounts, the combined measurement signal will have an AC component which can be measured and which is proportional to the difference in the amount of attenuation in the two amplitude modulated signals. This apparatus improves the accuracy of the absorption measurement in a gas analysis system but suffers from the requirement of precision mechanical modulation of separate energy signals and the difficulties concommittant therewith.

In addition, prior art devices generally use a single interrogation wavelength during the course of an investigation. To make measurement determinations at a plurality of wavelengths, it is generally necessary to replace either the energy source or the monochromatic filter being used, and to recalibrate the system accordingly. This procedure can prove both time consuming and inefficient.

In my application Ser. No. 178,190, referred to above, an apparatus and method for providing substantially improved sensitivity and reliability for photometric detection in fluids are described. In that apparatus, as well as in other dual component beam systems, as the sensitivity improves and approaches significantly low values, the apparatus is subject to inaccuracies due to the small effects such as for example, a change in energy source output, or different transmission or reflectance of various energy components due to changes of temperature, humidity, use, or other time dependent effects. These changes are not predictable and cannot be compensated for during the initial set up and calibration of the equipment. In addition, the erroneous results which can occur as a result of these time dependent changes in the relative signal amplitudes can provide both misleading and inaccurate results.

It is therefore a principal object of this invention to provide a detection and/or analysis apparatus and method with further improved precision by automatic compensation for changes as a result of time dependent mechanisms. Other objects of the invention are a fluid detection and/or analysis apparatus and method with reduced complexity, high efficiency, high reliability, and a relatively inexpensive manufacturing cost. A further object of the invention is a fluid detection and/or analysis apparatus and method which automatically compensate for relatively slow time varying changes in the component beams wherein the value of the time varying component is not predictable over time.

SUMMARY OF THE INVENTION

The invention relates to a photometric analysis apparatus for analyzing, in a fluid medium, at least one sample component having a characteristic absorbent wavelength of interest. The sample component may of course have more than one characteristic absorption wavelength of interest. The apparatus includes elements for forming at least first and second time varying component beams and a fluid sample chamber having an optical path passing therethrough, the chamber being positioned in the path of one of the beams of electromagnetic radiation, including radiation at least at the one characteristic wavelength, whereby the beam passes through the chamber along the optical path of the chamber. The invention features elements for measuring, at respective measurement positions, the first and second component beams, and circuit elements responsive to the measuring elements for varying, prior to the measurement positions, the relative intensities of the first and second component beams.

When the intensities of the component beams are measured, both the AC (that is, time varying) and DC (that is, background ambient) amplitudes can be determined. The apparatus therefore can maintain equal time-varying, AC, energy levels in the component beam, a constant DC total energy level for the component beams, and equal DC energy levels for the component beams individually.

In a particular embodiment, the invention relates to a photometric analysis apparatus for analyzing, in a fluid medium, at least one sample component of a sample fluid wherein the sample component has a characteristic absorption wavelength of interest. The apparatus has a beam modulation element in the path of a directed beam of electromagnetic radiation including radiation at at least the characteristic wavelength. The bean modulation element provides a first and a second component beam whose time-varying intensities vary 180° out of phase with each other at the rate of repetitive movement of the beam modulation element. The apparatus further has a sample fluid holding chamber which has a first optical path passing therethrough, the chamber being positioned in the path of one of the first or second component beams for passing that component beam through the sample chamber along the sample chamber optical path. A reference fluid holding chamber has a second optical path passing therethrough and the reference chamber is positioned in the path of the other of the first and second components for passing that other component beam therethrough along the reference chamber optical path. The apparatus further has a member for combining the first and second components after passage through the sample and reference chambers, and can have measurement elements for measuring or detecting the AC component, if any, of the combined beam.

The invention further features in this embodiment, a second measuring element for measuring the first and second component beams before the beams pass through the sample and reference chambers. Elements responsive to the second measuring device for varying the relative intensities of the first and second component beams prior to passing through the sample and reference chambers enable an improved analysis apparatus to be produced by maintaining a constant calibration thereof.

In one aspect, the beam modulation element features a planar member having a reflectance and a transmittance with respect to the directed beam which vary across its surface. A driver repetitively moves the planar member across the path of energy from the beam source and the driver moves in response to signals from the second measuring element for varying the center of movement of the planar member relative to the beam source incident energy.

The planar member, in a particular embodiment, is a substantially transparent substrate having a partially reflecting, non-absorbing coating thereon. The coating has a varying transmittance corresponding to a selected function of position on the substrate. The coating provides a corresponding varying reflectance of incident radiation.

In another particular embodiment, the invention relates to a photometric analysis apparatus for analyzing, in a fluid medium, at least one sample component having a characteristic absorption wavelength of interest. The apparatus has elements for forming at least first and second time-varying component beams and a fluid sample chamber having an optical axis passing therethrough, the chamber being positioned in the path of at least one of the beams of electromagnetic radiation including radiation at at least the one characteristic wavelength for passing the beam through the chamber along the optical axis. In this embodiment, the invention features elements for measuring at respective measurement positions the energy in the first and second component beams, the measuring elements being responsive to the sum of the DC energy in the beams and the sum of the AC energy in the combined beams. Further elements are provided, responsive to the measuring elements, for varying at a position prior to the measurement positions, the relative intensities of the first and second component beams, for equalizing the AC energy in the component beams and for maintaining the total DC energy substantially constant.

The invention further features a method for analyzing a fluid medium having at least one sample component. The component has a charactertistic absorption wavelength of interest. The method features the step of dividing an incident beam source of electromagnetic radiation, including radiation at at least the one characteristic wavelength of interest, for producing two time-varying components having a defined interdependent timevarying functional relationship. The method further features the steps of sampling the first and second component beams for determining the relative time-varying intensities of the beams; altering the relative intensity of said component beams in accordance with said sampled values for providing a predetermined functional relationship between the time-varying intensities of the component beams; directing at least one of the component beams through the fluid medium; combining the resulting beams; and measuring the time-varying components of the combined signal for determining energy absorption by the one sample fluid.

The method further features the steps of determining the intensity of the incident beam source of radiation and altering the intensity of said beam to maintain a constant beam intensity.

BRIEF DESCRIPTION OF THE DRAWINGS

Other objects, features, and advantages of the invention will appear from the following description of preferred embodiments of the invention and the drawings in which:

FIG. 2 is a graphical representation showing the respective amplitudes of the sample and reference beams and the resulting output of the detector in the absence of a sample gas differential absorption;

FIG. 3 is a figure similar to FIG. 2 showing the respective amplitudes of the sample and reference beams in the presence of sample gas differential absorption;

FIG. 6 is a schematic elevation view of the apparatus for oscillating the disk;

FIG. 7 is a view along lines 7—7 of FIG. 6;

FIG. 8 is a cross-sectional view of the disk along lines 8—8 of FIG. 7; and

FIG. 9 is a schematic view of the embodiment of FIG. 4 wherein one of the feedback systems is omitted.

DESCRIPTION OF PARTICULAR PREFERRED EMBODIMENTS

Figure 1:
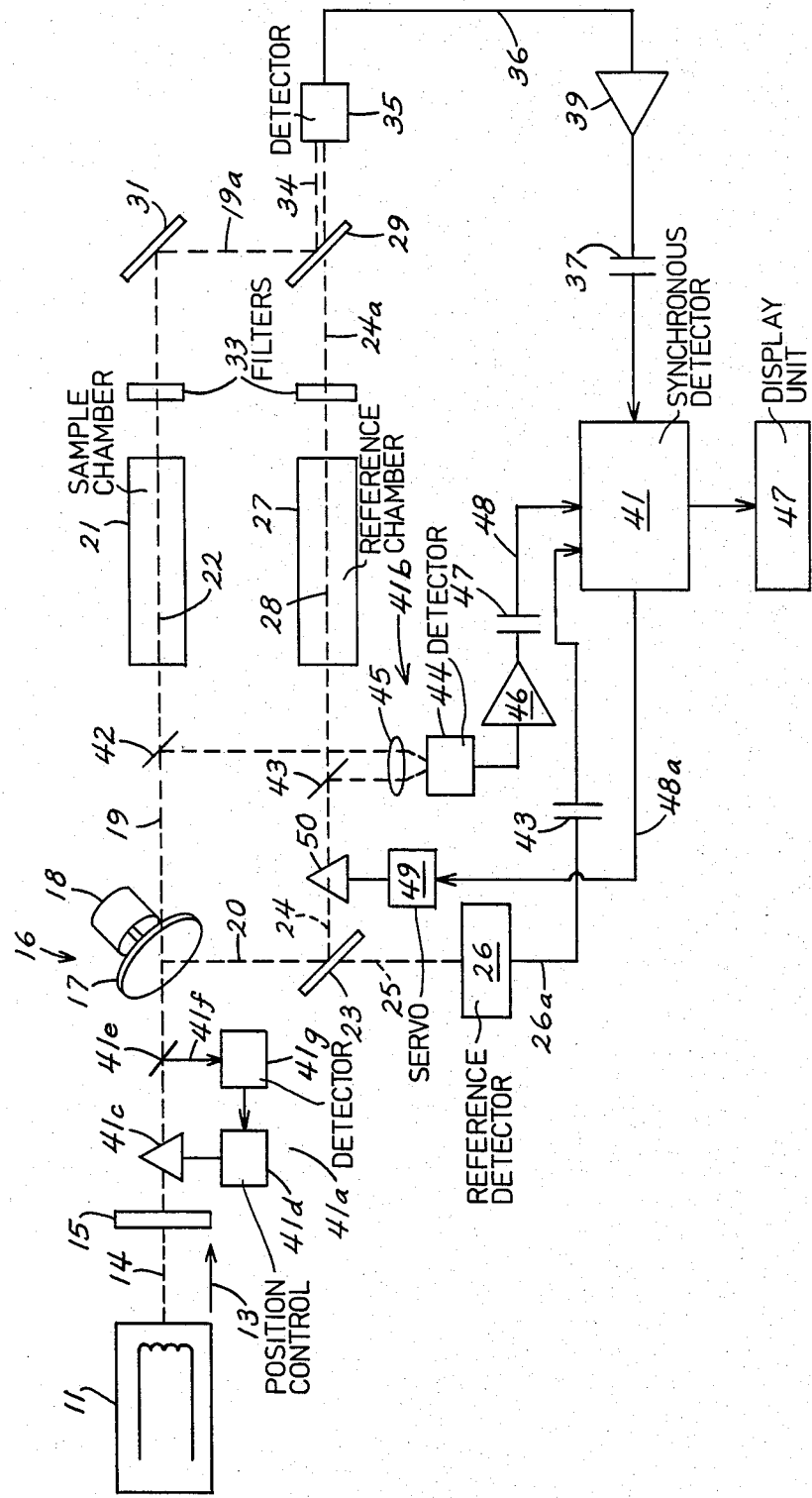
FIG. 1 is a schematic view of a gas detection and analysis apparatus in which the present invention is incorporated.

The photometric detection method and apparatus described herein can be advantageously employed in fluid detection systems, for example, a gas spectrometer or in liquid chromotography. Referring to FIG. 1, in a gas detection system, a source 11 of polychromatic infrared or other electromagnetic radiation directs a preferably collimated beam 14 outwardly in the direction of an arrow 13. The beam passes through a filter 15, which allows passage of only a narrow band of wavelengths, including a wavelength for which a gas to be investigated has a characteristic absorption.

The filtered beam is incident on a beam-modulation element 16. Illustrated element 16 has a planar disk-shaped member 17 which is oscillated or "dithered" sinusoidally by a driver element 18. Illustrated disk 17 is constructed (as described below in connection with FIG. 8) so that its transmittance and reflectance, at at least the wavelengths of interest, vary linearly with the angular position of the disk. For example, the disk surface may include a dielectric layer whose thickness, and accordingly its reflective properties, varies with angle. Preferably, the disk is also dielectric coated to reduce energy losses. Illustrated disk member 17 is oscillated at a sinusoidally varying angular velocity, as described below, although it will be clear to those practiced in the art that other combinations of speed relationships and disk member configurations can be employed.

The disk 17 divides the incident beam into a transmitted beam 19 and a reflected beam 20. Since the reflectance (R) and transmittance (T) are related by the equation $R = 1 - T$ (assuming negligible absorption by the disk, which is not a limitation of the apparatus), the variation in intensity of the reflected beam will be "oppositely directed" to that of the transmitted beam. Although the disk may be structured to produce any of a variety of mathematical relationships between the reflected and the transmitted beams, in this particular embodiment a sinusoidal relationship between the two is utilized. In other words, the amplitudes of the reflected and transmitted beams, when the disk is oscillated or "dithered" in the illustrated embodiment, vary sinusoidally, 180° out of phase with each other.

The transmitted, or sample, beam 19 is directed to and through a sample chamber 21 which encloses a sample of the gaseous medium being investigated. If one or more of the gases present in the sample chamber has an absorption characteristic at a particular wavelength of the incident radiation, the sample beam will be attenuated (a portion absorbed) during its passage through the sample chamber 21 along its optical path 22. The amount of attenuation will be proportional to the density of absorbing gas within the sample chamber and it is that attenuation which the apparatus is designed to accurately determine.

Meanwhile, the reflected beam 20 is directed onto a fixed beam splitter 23 which further divides the reflected beam into major and minor reference beams 24 and 25. The major reference beam 24 is reflected by the beam splitter 23, while the minor reference beam 25 is transmitted through the beam splitter and is incident upon a reference detector 26. The reference detector 26, a photodetector, produces, in response to incident minor reference beam 25, a time varying signal over a line 26a of the same fundamental frequency as the modulation frequency of the sinusoidally varying, reflected beam 20. That AC signal will be used during synchronous detection as described in more detail below. The major reference beam 24 is directed to and through a second, or reference, chamber 27, along its optical path 28. Chamber 27 is preferably identical in structure to the sample chamber 21, and contains a known reference gas which can include a known quantity of the gas to be investigated or detected.

At a beam combining element 29, which functions generally in the reverse manner of the beam splitter 23, an exiting reference beam 24a is combined with an exiting sample beam 19a, which in the illustrated embodiment has been reflected by a mirror 31 onto the beam combining element 29. When the beams 19a and 24a are combined, both beams will have traversed substantially identical optical paths, and the original 180° out of phase relationship will be maintained. More importantly, both beam will have the same atmospheric paths so that distortions occurring in one path, for example due to humidity, will also occur in the other path. Thus, when the attenuation in both optical paths is the same, which can under some circumstances be equated to the same quantity of sample gas in the sample and the reference chambers, the combined beam will, as described below according to the invention, have a constant intensity.

For example, assume that at position A the intensity of the original beam is $I_o$. The intensity of the transmitted portion (beam 19) (ignoring losses and assuming 100% modulation) will be $I_o(\frac{1}{2} + \frac{1}{2}\sin w_o t)$, where $w_o$ corresponds to the frequency of oscillation of the disk 17. The reflected portion (beam 20) will have an intensity $I_o(\frac{1}{2} - \frac{1}{2}\sin w_o t)$. Upon emergence from their respective chambers (and ignoring the losses at beam splitter 23), tne transmitted sample beam has an intensity $K_1 I_o(\frac{1}{2} + \frac{1}{2}\sin w_o t)$ and the reflected, reference beam has an intensity $K_2 I_o(\frac{1}{2} - \frac{1}{2}\sin w_o t)$ where $K_1$ and $K_2$ represent the attenuation of the respective beams in passing through the sample and reference chambers. If the attenuations are equal, or are somehow made equal ($K_1 = K_2 = K_o$), the combined beam will have an intensity equal to $K_o[I_o(\frac{1}{2} + \frac{1}{2}\sin w_o t) + I_o(\frac{1}{2} - \frac{1}{2}\sin w_o t)] = K_o I_o$, where $K_o$ is a constant, time-independent value. Thus, $K_o$ represents the attenuation, if any, in the chambers 21 and 27, when, for example, the sample and reference chambers are identical in structure and contain equal amounts of identical gases. (See FIG. 2 for a graphic representation of these relationships.)

Referring again to the illustrated embodiment of FIG. 1, variable neutral density filters 33 can be positioned in the paths of either or both of the exiting sample and the reference beams to balance their intensities during dynamic calibration of the apparatus, i.e., in a reference condition when both chambers 21, 27 contain selected amounts (which may be an empty condition) of the sample gas(es). That is, the intensity of one of the beams can be attenuated to compensate for transmission or absorption losses in the other beam, to insure that for the standard reference condition, a constant intensity is achieved upon combination of the beams to form beam 34. For example, the intensity of the exiting sample beam 19a can be attenuated to compensate for the slight loss in the reflected beam 20 at beam splitter 23, or alternatively the reference beam might be attenuated to compensate for slight absorption in the modulator disk.

The combined beam 34 is directed onto a conventional photosensitive element 35, for example an infrared photodetector when infrared radiation is employed, which produces an electrical current output over a line 36, proportional to the intensity of the radiation incident thereon. In the case of a constant intensity beam, the output of the detector will be a constant current. A different situation exists when there is a quantity of sample gas in the sample chamber 21 which effects a different amount of absorption compared to the gas which was in sample chamber 21 during calibration of the system. Using the same assumptions as recited above regarding the intensity of the initial radiation, the intensity of the beam emerging from the sample chamber can be characterized as $KI_o(\frac{1}{2}+\frac{1}{2}\sin w_o t)$ where K is a positive factor less than unity and different than $K_o$. Thus, the intensity of the recombined beam incident upon the detector will no longer be constant but will be represented by $[KI_o(\frac{1}{2}+\frac{1}{2}\sin w_o t)+I_o K_o(\frac{1}{2}-\frac{1}{2}\sin w_o t)]=\frac{1}{2}I_o[(K+K_o)+(K-K_o)\sin w_o t]$ (see FIG. 3). This recombined beam thus has a time varying amplitude component, an AC component intensity $(\frac{1}{2}I_o[(K-K_o)\sin w_o t])$, superimposed on the DC signal component of intensity $\frac{1}{2}(K+K_o)I_o$. The AC component represents the difference between the gaseous medium being measured and the reference value employed during system calibration. It is therefore that AC value which carries the information of interest and the AC component output from the detector can be measured accurately using amplification and synchronous detection techniques as follows.

Still referring to FIG. 1, the output of detector 35 is applied to an amplifier 39. The output of amplifier 39 is coupled through a capacitor 37 to a synchronous detector 41. The synchronous detector 41 also receives the AC component of the output signal from the reference detector 26 through a second coupling capacitor 43. The synchronous detector 41 thus synchronously detects the AC component of the signal from the detector 35 and produces, for example, a DC output level proportional to the amplitude of the information AC signal from amplifier 39, to drive a display unit 47 such as, for example, an X-Y plotter or a digital readout. The display unit indicates at least the amplitude of the AC component in the output of detector 35. Clearly in the case of a pure DC output from the detector 35, the first coupling capacitor 37 will block passage of the DC signal to the synchronous detector 41, resulting in a detector output indicating a "zero" AC component.

Figure 4:
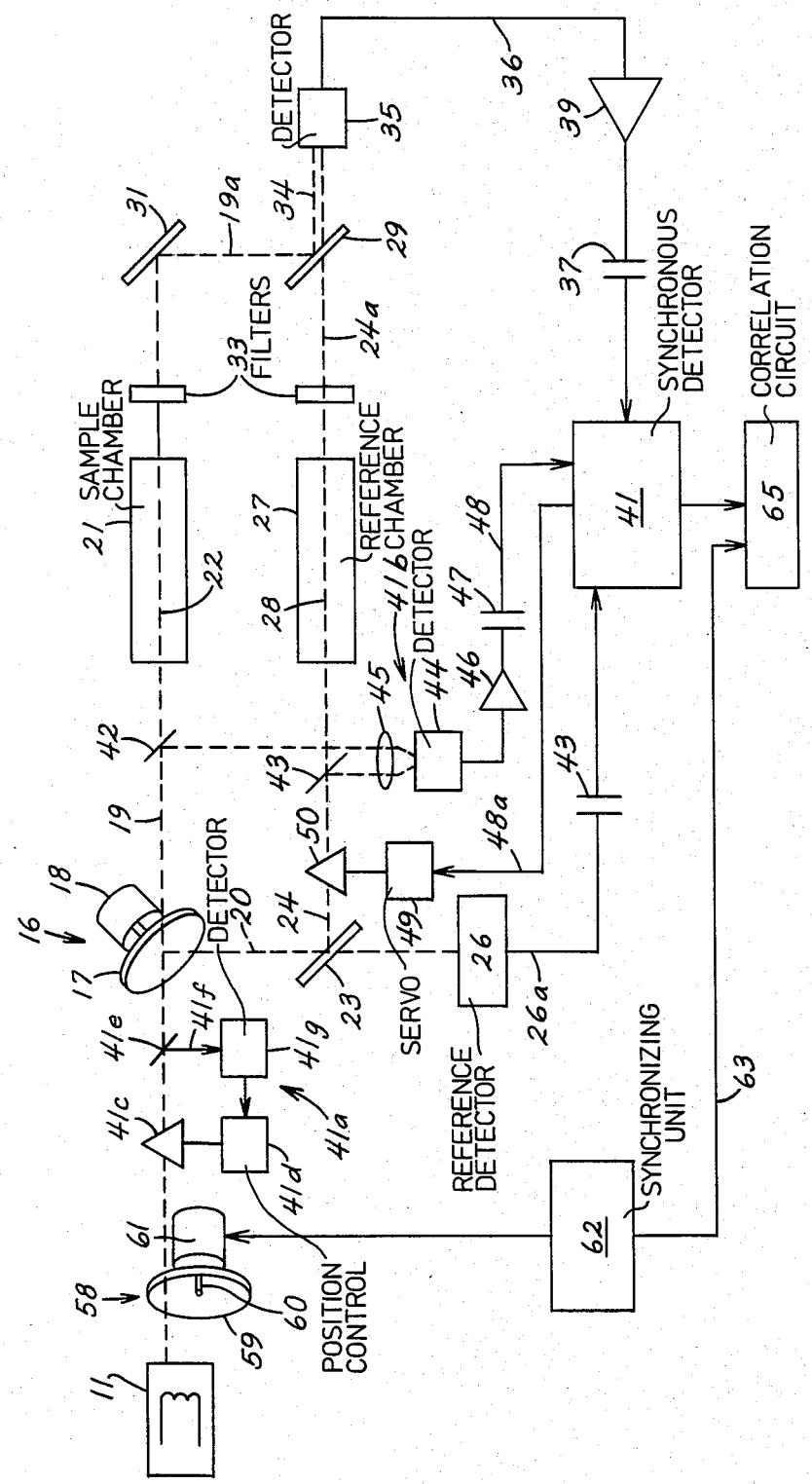
FIG. 4 is a schematic view of a second embodiment of a gas detection and analysis apparatus in which the present invention is incorporated.
Figure 5:
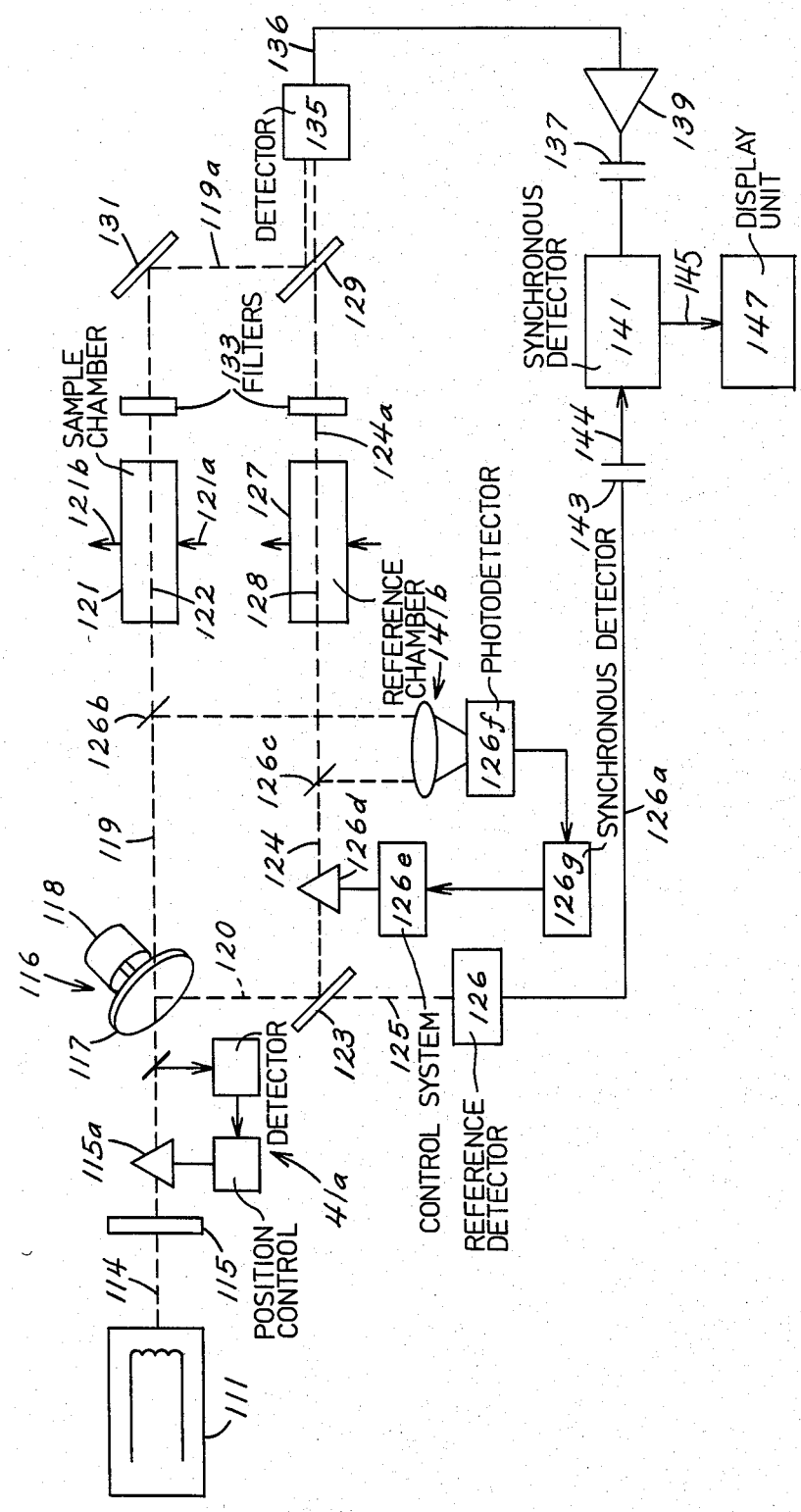
FIG. 5 is a schematic view of an ultraviolet detector according to the invention for use in liquid chromatography.

With regard to the embodiment of FIG. 1, it should be noted that although the beam which was reflected by the disk was utilized as the reference beam and the beam transmitted through the disk was utilized as the sample beam, the reverse situation also would work equally well. Further, all optical surfaces in this illustrated embodiment, and in the embodiments illustrated in FIGS. 4 and 5, are preferably treated with an anti-reflection coating to avoid the generation of erroneous energy beams.

Until now, it has been somewhat implicitly assumed that the beams forming the combined beam 34 which is received by detector 35, have, once filters 33 are adjusted properly, equal time varying intensitites, constant over time, so long as the calibration conditions are maintained in the sample chamber 21 and the reference chamber 27. This, however, need not be the case. Thus, there may be time, humidity and/or temperature variations in the energy source output, the absorption qualities of the modulator disk 17, or other time, humidity and/or temperature dependent phenomena, which cause the apparatus to have a time varying response either over the short or long term.

The illustrated apparatus of FIG. 1 therefore further has two independent automatic feedback control systems 41a, 41b, each of which varies the operating point of an associated attenuation filter to provide input component beam signals to the sample and reference chambers which are substantially time-invarient in amplitude. The feedback control system 41a is employed to control the intensity of energy from source 11 incident upon the modulation element 16. This system 41a can be self-contained. The system employs a variable density element, for example wedge 41c, which can be mechanically moved in the path of beam 14 by a mechanical position control element 41d. The light energy passing through attenuation element 41c is directed to a beam splitter 41e wherein a small portion of the incident energy is reflected along a path 41f toward a photodetector 41g. The output of the photodetector 41g is applied to the position control element 41d. Thereby, the position of attenuation element 41c is mechanically controlled, in this embodiment, by the feedback control loop, to provide a constant amplitude energy signal to modulation element 16. Apparatus for accomplishing control of the source energy, by controlling the lamp electrical current, is well known in the art.

The other feedback control system 41b of the illustrated embodiment employs a first beam splitting mirror 42, in the path of beam 19, and a second beam splitting mirror 43, in the path of beam 24. These beam splitting mirrors pass about one-half of the energy incident thereon and reflect, respectively, about one-half of the energy to a photodetector 44. A lens system 45 can be provided if desired to direct the light energy more uniformly over coincident areas of the photodetector. The photodectector can be any of a plurality of detection systems, as is well known in the art, including, for example, a photomultiplier tube or a semiconductor photodetector element. Preferably photodetectors 35 and 44 are identical.

The combined output of the detector 44 should, according to the invention have no AC component when the two input signals are equal in modulation amplitude. The output of the photodetector is connected to an amplifier circuit 46, and is coupled through a capacitor 47, over a line 48, to the synchronous detector 41. An output of the synchronous detector 41 over a line 48a, in response to the input over line 48, is employed to control an electromechanical servo device 49 to move an attenuation device, for example, a neutral density wedge 50, into and out of the path of one of the component beams, here shown to be beam 24. (Other variable density element configurations could be used.) Thus, the wedge position is adjusted so that the attenuation of beam 24 provides an equalization of the AC signal components entering the sample and reference chambers.

The wedge 50 is preferably a variable neutral density filter having a transmission which varies linearly along one dimension. In one preferred embodiment, it is a 6° borosilicate glass wedge with an anti-reflection coating for use with visible wavelengths. The wedge is moved into and out of the path of the beam along that one dimension and varies the overall intensity of the beam passing therethrough. The synchronous detector and feedback circuitry 41b are adjusted to provide a stable operating system which, once initial calibration is attained, provides, over time and despite temperature and humidity changes, equal modulation signal inputs to the sample and reference chambers. This automatic adjustment occurs independently of the remaining measurement circuitry and becomes important due to the very high sensitivity of the apparatus disclosed herein.

The preferred embodiments hereinbefore and hereinafter to be described enable the measurement and analysis of a gaseous medium by measuring the difference in attenuation between a reference signal and an unknown signal. The apparatus and method can also be employed simply to detect the presence of one or more specified gas components in the gaseous medium in which case the elements which measure the value of the difference would not be required and only the phase (or in some cases, the presence) of the AC component in the combined signal need be detected.

Referring now to FIG. 4, a second embodiment of the present invention offers advantages in searching at multiple wavelengths of interest, for example for multiple gases within a given gaseous sample. In this second embodiment, a spectrophotometer, has a filtering element 58, in the illustrated embodiment having a disk 59 coupled by a shaft 60 to a driver 61, inserted between the source 11 and the beam-modulation element 16. The monochromatic filter 15 (FIG. 1) has been removed.

The disk 59 functions as a multiple passband filter in that the passband changes with the angular position of the disk. The band of wavelengths transmitted therethrough can be changed in either a continuous or preferably a discrete mode (or even a combination thereof); and so long as a well-defined relationship exists between the band of wavelengths and, in the illustrated embodiment, the angular position of the disk 59, a precise relationship can be maintained corresponding to the wavelengths passed by the filter as a function of time.

The remainder of the apparatus in this embodiment corresponds substantially to the embodiment of FIG. 1. The radiation transmitted through to the disk 17 is processed identically as was the substantially monochromatic beam of FIG. 1. In effect, however, the apparatus of FIG. 4 will perform a sequence of identical measurement or detections, each at a different wavelength of interest. A synchronizing unit 62 responsive to the position of filter element 58 provides an electrical reference signal over a line 63 to the electronic circuit 65 to correlate the information signal being provided by the synchronous detector 41 to the wavelength of radiation being passed by element 58. Synchronizing unit 62 thus indicates when the element 58 has made a transition from one wavelength of interest to another (in the discrete mode of operation), and unit 62 can be any of a variety of well known devices, such as, for example, a photosensor which senses markers appropriately positioned on the surface of the disk element 58, and which produces distinctive outputs in response thereto. Alternatively the synchronizing unit can employ a shaft position encoder coupled to the shaft 60. The output of the encoder identifies the angular position of the shaft, and therefore the wavelength that is passed at that position.

If the reference gas has different absorption characteristics at the different wavelengths of interest, these differences must be measured, and thereafter taken into account during calibration of the apparatus. In particular, then, circuit 65, in response to the detected differential between the sample and reflected beams, will produce an output which accurately represents the amount of relative attenuation by the sample gas at each wavelength. For example the circuit 65 may employ several subcircuits, each corresponding to a different wavelength of interest, which are sequentially addressed or selected by the synchronizing unit 62 reference signals over line 63. Each subcircuit, in its turn, generates an output for the display appropriate for the detected signal at that wavelength.

It is thus especially important here, where a plurality of different elements are employed in the system, to provide known input signals to the sample and reference chambers. The feedback control systems 41a, 41b therefore operate with each of the wavelengths of interest and provides the necessary equalization (if any is needed) to ensure that equal amplitude signals are input to the sample and reference chambers. This can be especially important since the absorption/reflection and transmittance properties of the various optical elements, and especially the disk 17, can easily vary as a function of wavelength. Thus, once the system is initially calibrated, the feedback control system automatically and continuously provides the necessary adjustment, if any, to effectively maintain that calibration. It is important to note that the two independent feedback control loops, 41a and 41b, automatically compensate for irregularities in the construction of filter disk 59. Thus, if the energy passing through disk 59 changes from wavelength to wavelength because, for example, of an irregularity in the spectrum of the combination of filter and source, the control loop 41a will provide, within the dynamics of the loop, a constant energy incident upon disk 17. In addition, the second control loop 41b provides equal amplitude modulation intensities entering the sample and reference chambers. Thus, the system, once calibrated, can be considered calibrated for all purposes.

The embodiments described thus far have all related to fluid photometric detection apparatus employing gases as the unknown or sample fluid. As noted above, the photometric detection systems with which the invention can be advantageously employed, are not limited to gas systems but also include liquid systems, for example ultraviolet absorption detectors for use in high speed liquid chromatography. The invention can be advantageously employed in these other fluid detection systems for providing superior detection and analysis capability.

Referring to FIG. 5, an ultraviolet absorption detector for use in liquid chromatography resembles substantially identically the gas detection apparatus of FIG. 1. The illustrated liquid chromatography system has a source 111 of polychromatic energy including energy at least in the ultraviolet range. The source directs its radiation, preferably in a collimated beam 114, toward a filter 115 which allows passage of only a narrow band of wavelengths. Included within that band is a wavelength to which the liquid being examined has a characteristic absorption. The filtered beam passes through a controlled attenuation filter 115a, and is incident on a beam modulation element 116. As in earlier embodiments, the illustrated element 116 has a planar disk shaped member 117 which is driven sinusoidally by a driver 118. The illustrated disk 117 is constructed so that its transmittance and reflectance, at wavelengths of interest, vary linearly with the angular position of the disk and thus sinusoidally when the disk is oscillated sinusoidally. In one embodiment, the disk has deposited multiple dielectric layers, alternating in dielectric constant; and accordingly its reflective properties vary linearly with the angular position of the disk over a selected range of oscillation. A maximum range of modulation between $\pm 40\%$ is typical for a multilayer dielectric coated disk. The disk is coated with another dielectric composition to reduce energy losses.

The disk 117 divides the incident beam into a transmitted beam 119 and a reflected beam 120. Thus, beams 119 and 120, as described in connection with the embodiment of FIG. 1, vary in intensity so that the reflected beam will be "oppositely directed" in modulation amplitude to the intensity of the transmitted beam. The transmitted, or sample beam 119 is directed to and through a sample chamber 121 which houses the liquid medium being investigated. Typically, chamber 121 has an inlet port 121a and an outlet port 121b into which and out of which, respectively, the liquid being examined flows.

In a typical system, as is well know in the art, a Z configuration sample chamber can be used. This is a classical type of chamber in which the mobile phase comes in one end of the chamber, sweeps the window, and goes down the cell cavity and out the other end. To minimize noise and drift due to flow variations, however, an H cell configuration can also be used. If one or more of the fluid components present in the sample chamber has an absorption characteristic at a particular wavelength of the incident radiation, the sample beam will be attenuated (corresponding to a portion of it being absorbed) during its passage through the sample chamber 121 along an optical path 122. The amount of attenuation in the liquid system, as in the gaseous system, will be proportional to the density of the absorbing fluid components within the sample chamber, and it is that attenuation which the apparatus is designed to accurately detect.

At the same time, the reflected beam 120 is being directed onto a fixed beam splitter 123 which further divides that beam into major and minor reference beams 124 and 125 respectively. The major reference beam 124, the reflected beam, is directed toward a reference chamber 127. The minor reference beam 125 is directed to a reference detector 126. The reference detector 126, typically a photodetector (sensitive to ultraviolet in this embodiment), produces in response to the minor reference beam 125 a signal having an AC signal component over a line 126a of the same frequency as the modulating frequency of the sinusoidally varying reflected beam 120. That AC signal, as described above, is used for synchronously detecting the AC component of what will become the combined output of the system.

As noted above in connection with the FIG. 1 and FIG. 2 embodiments, feedback control apparatus are employed to ensure that the signals entering the chambers 121 and 127 are equal in DC amplitude and percent modulation. As described in connection with the FIG. 1 counterpart embodiment, a feedback control system 141b employs a pair of beam splitting mirrors 126b, 126c, an attenuation device 126d (for example a neutral density wedge) controlled by a control system 126e, a photodetector 126f and a synchronous detector 126g responsive to the photodetector for providing the control signal for the control element 126e to vary the position of the attenuation wedge 126d in the path of beam 124. Thus, with the system initially calibrated, the precision of the apparatus is maintained so that the AC intensities of the signal entering chambers 121 and 127 are constant. (Control of the beam source energy incident upon disk 117 can be controlled by a feedback apparatus corresponding to feedback system 41a of FIG. 1.)

As noted above, the major reference beam is directed toward the reference chamber 127 and in particular an optical path 128 through the reference chamber. Reference chamber 127 is preferably identical in structure to the sample chamber 121 and contains a known reference fluid which can include a known quantity of the fluid component(s) to be investigated or detected.

An exiting reference beam 124a is combined with an exiting sample beam 119a which, in the illustrated embodiment, has been reflected by a mirror 131 onto the beam combining element 129. When beams 119a and 124a are combined, both beams will have traveled substantially the same length paths and will have suffered substantially the same attenuation due to the naturally occurring attenuating factors in the field through which the beams pass. The beams are directed onto a photodetecting element 135 which is, in the illustrated embodiment, an ultraviolet sensitive photodetector and which produces an output over a line 136 which is proportional to the intensity of the radiation incident thereon. As in the embodiment of FIG. 1, it may be desirable to provide additional filtering such as neutral density filters 133 to equalize the time varying components of the system so that the output of the detector 135 has no AC component when the densities of the sample liquids being examined in the reference and sample chambers 127 and 121 respectively are equal.

The output of detector 135 over line 136 is applied directly to an amplifier 139. The output of amplifier 139 is applied to a synchronous detector 141 through a capacitor 137. Detector 141 also receives the AC component from reference beam 125 through a second coupling capacitor 143 over a line 144. The synchronous detector 141 thereby, as described in connection with FIG. 1, synchronously detects the AC component of the signal from the detector 135 and produces an output over a line 145 proportional to the amplitude of the information AC signal component from amplifier 139. That output drives a display unit 147. The display unit thus indicates at least the amplitude of the AC component in the output of detector 135. It is this AC component which provides a measure of the sample liquid component being examined (or samples being examined) in the sample chamber 121.

It should be evident that this embodiment is substantially identical to the embodiment of FIG. 1. In a similar manner, the embodiment described in connection with FIG. 4 can also be adapted to a liquid detection system for use in high speed liquid chromotography. Thus, in the embodiment of FIG. 4 the sample and reference chambers 21 and 27 can be made to correspond respectively to the chambers 121 and 127 of FIG. 5.

Referring to FIG. 6, according to one particular embodiment of the invention, the disk 17 is connected through a shaft 150 to the "dither" or oscillating control driver 18. The driver 18 is responsive to signals over lines 152 for oscillating shaft 150 according to a sinusoidal function. Thus the angular position of shaft 150 varies as "sin $w_o t$". The DC level of the input signal over line 152 acts to control and set the center of the angular rotation of shaft 150 and once set, is, for the embodiments illustrated in FIGS. 1 and 5, a constant value. In other embodiments, the center position can be varied as described in detail below.

The illustrated disk 17, referring to FIGS. 7 and 8, has an area 154 of reflectance and transmittance which, in the preferred embodiment, vary linearly in value with the angular position of the disk. Thus, for example, at one circumferential end of area 154, along for example a radius 156, the transmittance can be substantially one hundred percent and the reflectance substantially zero while at the other end of area 154, along a radius 158, the transmittance can be substantially zero and the reflectance, substantially one hundred percent. When this disk is oscillated by the driver 18, according to the sinusoidal function noted above, the reflected and transmitted beam outputs, if the extent of sinusoidal oscillation extends fully from the angular position bounded by radius 156 to the angular position bounded by radius 158, have a full one hundred percent modulation. A lesser angular oscillation provides a smaller percentage of modulation.

Referring to FIG. 8, the illustrated disk 17 has a quartz substrate 160, anti-reflection coatings 162 and 164 on either side of the quartz substrate, and a ramp-like reflectance/attenuation coating 166 to provide the required reflectance/transmitter function according to a preferred embodiment of the invention. The coating 166 has a linearly varying thickness with respect to the angular position of the disk. The transmittance of the coating is proportional to its thickness and the reflectance of the coatings is substantially (ignoring losses due to absorption) one minus the transmittance. Thus, using a disk such as that shown in FIG. 8, and by varying the center of sinusoidal oscillation of the disk, from for example the position indicated by axial line 170 to the position indicated by axial line 172, keeping the amplitude of oscillation (i.e. the percentage of modulation) constant, the effect is to reduce the transmitted DC component while increasing the reflected DC component. In effect then, by accepting less than one hundred percent modulation, the relative intensities of the DC components directed to the sample and reference chambers can be varied, in this embodiment, by shifting the center of oscillation of the disk (the AC component remaining constant). This can be achieved by modifying the DC signal level on line 152 (which controls the center position of oscillation of disk 17) as described in more detail in connection with FIG. 10.

As described in more detail in copending U.S. application Ser. No. 312,911, filed Oct. 19, 1981, for a Low Noise Amplifier and Method for Energy Biased Radiation Sensitive Receiver, a photodetector/amplifier configuration which employs for example a semiconductor photodiode, will be optimized for a single power level incident thereon (the frequency remaining constant). It is therefore advantageous to control the power level incident upon the photodiode, the DC level described hereinabove, whenever possible. Unfortunately however, in the case of the FIG. 4 embodiment wherein different source wavelengths are employed, the reflective surface of disk 17 will have a reflectance which generally varies as a function of the incident energy wavelength. Therefore, as different wavelengths are employed, the magnitude of the reflected and hence of the transmitted signals will vary. As a result, the component beams 19 and 20 of FIG. 4, which preferably have equal, predetermined DC amplitudes, will generally, as the wavelength changes, have different DC amplitudes. Consequently, if the feedback circuit 41b of FIG. 4 is adjusted to equalize the AC components, i.e. the modulation component of the optical signals, it will generally occur that the DC components will not be equal, and further that the sum of the DC components will vary as the wavelength of incident energy changes. Consequently, the average power incident upon detectors 35 and 44 will change and the system will no longer be "optimized" to provide a maximum signal to noise figure.

The feedback compensation circuit 41a of FIG. 4 provides only limited help. This circuit configuration is directed to ensuring that the energy incident upon the disk remains constant. The circuit 41a does not compensate for the difference in the ratio of energy being reflected by the disk and the energy passing through the disk. Consequently, a different feedback control system is desireable in order to maintain the energy and modulation percentage of component beams 19 and 20 equal and constant.

Referring then to FIG. 9, the embodiment of FIG. 4 is modified by eliminating the feedback system 41a and modifying system 41b as follows. In addition to employing the photodetector 44, whose output represents the sum of the sampling of beams 19 and 24, two additional photodetectors are employed for sampling the individual signals representing the intensity of the energy in beams 19 and 24. As shown in FIG. 10, a photodetector 200 receives a fixed fraction of beam 19 from a beam splitting mirror 201. Photodetector 200 is connected to an amplifier 204 whose output is coupled to a comparison and summing circuit 206. Similarly, the output of a photodetector 202 (responsive to a fixed fraction of beam 24 from beam splitting mirror 207) is connected to an amplifier 208 whose output is also coupled to the circuit 206. As a result, circuit 206 measures the sum and the difference of the DC amplitude of the outputs of detectors 200 and 202 for determining whether the DC amplitude sum is constant and whether the difference is at a null. As a result of these measurements, circuit 206 controls the position of the center of oscillation for disk 17 over line 152 and the position of variable density element 115a by a signal over line 210; and synchronous detector 41 controls the position of wedge 50 in order to maintain, together, a constant total DC amplitude for the combined beams, and equal AC and DC amplitudes in the component beams 19 and 24. In this manner, each of the photodetecting circuits is always operating at peak sensitivity, which enables the apparatus to maintain an extremely high sensitivity to changes in the gases being analyzed.

In the illustrated and preferred embodiment of the apparatus and method according to the invention, electromechanical servo feedback systems have been employed. While these systems are designed to operate independent of one another, care must be taken to avoid adverse interaction between the feedback "loops". Thus, according to the preferred embodiment of the invention, and referring to FIG. 9 as a typical example, the feedback mechanism associated with system 41b is designed to have a significantly shorter response time than the feedback system associated with either the disk control unit or the directed beam control system 41a. With respect to those two systems, the time constant for the disk control unit is selected to be significantly shorter than that for the beam control mechanism 41a. Thus, system 41b can have, according to the invention, a time constant on the order of one tenth of a second, the control for disk 17 can have a time constant on the order of one second, and the control system 41a for movement of a wedge 115a can have a time constant on the order of for example ten seconds. In this manner, interaction between the various feedback control loops is avoided.

While each of the control loops for ensuring precise determination of the measured values in the apparatus are electromechanical in nature, similar results can be obtained by employing a microprocessor as follows. The microprocessor can be programmed to operate upon the output signal and to compensate that measured output for changes in the operating parameters of the apparatus. Thus, the system could for example make a pre-measurement calibration of all of the photodetectors and associated electronics. Thereafter, after the measurements of the gas have been made, the apparatus would make a post-measurement calibration. The microprocessor would then apply an appropriate correction factor to the measured data. While this provides a significantly reduced mechanical control system, it does not enable the system to adjust for varying parameters which occur during a measurement; nor does it provide for optimizing the photodetectors by maintaining the DC intensities the same. Thus, even if a microprocessing system were employed, it is likely that the center position of the modulation disk 17 would still be controlled in an electromechanical feedback configuration.

While it has been assumed that an electromechanical feedback configuration would be required for the polychromatic spectrometer of FIG. 9, it is also possible to make a pre-measurement calibration of the reflectance wheel 17 with respect to each of the monochromatic wavelengths being employed, in connection with filter wheel 59, and thereby either mechanically or electrically connect or correlate the position of the filter wheel and the center position of the oscillating disk 17. Such a "connection" can be implemented either mechanically or electrically as would be well within the skill of those practiced in the art.

The illustrative embodiments of the figures each describe a complete detection and analysis apparatus and method. However, subassemblies of the illustrated detection and analysis apparatus and method can be used in existing analysis and/or detection apparatus as described herein to upgrade an existing apparatus. Thus, as various changes can be made in the embodiments set forth above without departing from the scope of the invention, it should be understood that the above description, including the accompanying drawings, shall be interpreted as illustrative and not in a limiting sense. Additions, subtractions, deletions and other modifications of the illustrated embodiments would be obvious to one practiced in the art and are within the scope of the following claims.

What is claimed is:

1. A photometric analysis apparatus for analyzing a fluid medium having at least one sample component having a characteristic absorption wavelength of interest, comprising:
   a beam source of electromagnetic radiation including radiation at at least said one characteristic wavelength for providing a directed beam containing said characteristic wavelength,
   beam modulation means in the path of said beam for providing first and second component beams, said beams having respectively time-varying portions whose intensities vary 180° out of phase at the rate of change of said beam modulation means,
   a sample fluid holding chamber having a first optical path passing therethrough, said sample chamber being positioned in the path of one of said component beams for passing said one component through said sample chamber along the sample chamber optical path passing therethrough,
   a reference fluid holding chamber having a second optical path passing therethrough, said reference fluid chamber being positioned in the path of the other of said first and second component beams for passing said other component beam through said reference chamber along the reference chamber optical path passing therethrough,
   means for combining said first and second component beams after passage through said sample fluid holding chamber and said reference fluid holding chamber,
   first means for measuring the AC component of said combined beam,
   second means for measuring said first and second component beams before said beams pass through said sample and reference chambers, and
   means responsive to said second measuring means for varying the relative intensities of said first and second component beams prior to passing through said sample and reference chambers.

2. A photometric analysis apparatus for analyzing a fluid medium having at least one sample component having a characteristic absorption wavelength of interest, comprising:
   a beam source of electromagnetic radiation including radiation at at least said one characteristic wavelength for providing a directed beam containing said characteristic wavelength,
   beam modulation means in the path of said beam for providing first and second component beams, said beams having respectively time-varying portions whose intensities vary 180° out of phase at the rate of change of said beam modulation means, the beam modulation means comprising
     a planar member having a reflectance and transmittance with respect to said directed beam which vary across its surface, and
     means for repetitively moving said member across the path of energy from the beam source for providing said first and second component beams,
   a sample fluid holding chamber having a first optical path passing therethrough, said sample chamber being positioned in the path of one of said component beams for passing said one component through said sample chamber along the sample chamber optical path passing therethrough,
   a reference fluid holding chamber having a second optical path passing therethrough, said reference fluid chamber being positioned in the path of the other of said first and second component beams for passing said other component beam through said reference chamber along the reference chamber optical path passing therethrough,
   means for combining said first and second component beams after passage through said sample fluid holding chamber and said reference fluid holding chamber,
   first means for measuring the AC component of said combined beam,
   second means for measuring said first and second component beams before said beams pass through said sample and reference chambers, and
   said repetitive moving means being responsive to said second measuring means for varying the center of movement of said planar member relative to said beam source incident energy for varying the intensities of said first and second component beams.

3. The apparatus of claim 2 wherein
   said second measuring means is responsive at least to the DC level of the combined energy of the beams, and further comprising
   means for changing the intensity of the beam incident on said modulation means.

4. The photometric analysis apparatus according to claim 2 wherein said planar member comprises
   a substantially transparent substrate, said substrate having a first coating on a first surface of said substrate having a varying transmittance corresponding to a selected function of position on said substrate, said coating providing a corresponding varying reflectance of incident radiation.

5. The photometric analysis apparatus of claim 1 wherein said varying means comprises
a neutral density material having a transmittance which varies along an actuating direction according to a predetermined function, and
a driver means responsive to said second measuring means for moving said material along said actuation direction in the path of one of said component beams for selectively attenuating the component beam.

6. The photometric analysis apparatus of claim 1 wherein said second measuring means comprises
a photodetector,
means in the path of each of said component beams, prior to the passage of said component beams through said sample and reference chambers respectively, for diverting a fixed fraction of said beams toward said photodetector,
means for measuring the output of said photodetector for determining the relative amplitude of the time-varying energy in said first and second component beams.

7. The apparatus according to claim 6 wherein said second measuring means includes means for synchronously detecting the time varying component in the output of the photodetector.

8. The apparatus of claim 7 wherein said second measuring means comprises means responsive to the synchronous detector means for providing an output signal to a driver means for maintaining equal amplitude time-varying component portions at the modulation frequency of interest.

9. The apparatus of claim 1 further comprising
third means for measuring the intensity of said beam source incident upon the beam modulation means, and
means responsive to said third measuring means for maintaining constant the intensity of energy incident upon said beam modulation means.

10. The apparatus of claim 9 wherein said maintaining means comprises
a variable density element,
means responsive to said third measuring means for positioning said element in the path of said beam source, and
said third means measures the energy of said beam source after it passes through said element.

11. A photometric analysis apparatus for analyzing a fluid medium having at least one sample component having a characteristic absorption wavelength of interest, comprising:
a beam source of electromagnetic radiation including radiation at at least said one characteristic wavelength for providing a directed beam containing said characteristic wavelength,
beam modulation means in the path of said beam for providing first and second component beams having time-varying portions whose intensities vary 180° out of phase at the rate of change of said beam modulation means,
a sample fluid holding chamber having a first optical path passing therethrough, said sample chamber being positioned in the path of one of said component beams for passing said one component through said sample chamber along the sample chamber optical path passing therethrough,
a reference fluid holding chamber having a second optical path passing therethrough, said reference fluid chamber being positioned in the path of the other of said first and second component beams for passing said other component beam through said reference chamber along the reference chamber optical path passing therethrough,
means for combining said first and second component beams after passage through said sample fluid holding chamber and said reference fluid holding chamber,
first means for measuring the AC component of said combined beam,
second means for measuring the intensity of said component beams, and
means responsive to said second measuring means for maintaining constant the combined energy of said component beams.

12. The apparatus of claim 11 wherein said maintaining means comprises
a variable density element, and
means responsive to said second measuring means for positioning said element in the path of said beam source.

13. In a photometric analysis apparatus for analyzing, in a fluid medium, at least one sample component having a characteristic absorption wavelength of interest, said apparatus comprising:
means for forming at least first and second time-varying component beams,
a fluid sample chamber having an optical path passing therethrough, said chamber being positioned in the path of at least one of said beams of electromagnetic radiation, including radiation at least at said one characteristic wavelength for passing said beam through said chamber along said optical path,
the improvement comprising
means for measuring at respective measurement positions said first and second component beams, and
means responsive to said measuring means for varying, prior to said measurment positions, the relative intensities of said first and second component beams.

14. The photometric analysis apparatus according to claim 13 wherein said beam forming means comprises
a beam source of electromagnetic radiation including radiation at at least said one characteristic wavelength for providing a directed beam containing said characteristic wavelength,
a planar member having a reflectance and transmittance with respect to an incident beam from said beam source which vary across its surface,
means for repetitively moving said member across the path of said incident beam, and
said repetitive moving means being responsive to said measuring means for varying the center of movement of said planar member relative to said incident beam whereby the relative intensities of said component beams vary.

15. The photometric analysis apparatus according to claim 14 wherein said planar member comprises
a substantially transparent substrate, said substrate having
a first coating on a first surface of said substrate having a varying transmittance corresponding to a selected function of position on said substrate, said coating providing a corresponding varying reflectance of incident radiation.

16. The photometric analysis apparatus of claim 13 wherein said varying means comprises
   a neutral density material having a transmittance which varies along an actuation direction according to a predetermined function, and
   a driver means responsive to said measuring means for moving said material along said actuation direction in the path of one of said component beams for selectively attenuating the component beam.

17. The photometric analysis apparatus of claim 13 wherein said measuring means comprises
   a photodetector,
   means in the path of each of said component beams for diverting a fixed fraction of said beams toward said photodetector,
   means for measuring the output of said photodetector for determining the relative amplitudes of the time-varying energy in said first and second component beams.

18. The apparatus of claim 17 wherein said determining means includes electrical filtering means for
   filtering the output of said photodetector to eliminate signal frequencies other than the modulation frequency of interest.

19. The apparatus according to claim 17 wherein said determining means includes means for synchronously detecting a time-varying signal component in the output of the photodetector.

20. The apparatus of claim 19 wherein said first measuring means comprises means responsive to the synchronous detector means for providing an output signal to a driver means for maintaining equal amplitude time-varying component portions at the modulation frequency of interest.

21. In a fluid analysis apparatus for analyzing, in a fluid medium, at least one sample fluid, said medium having a characteristic absorption wavelength of interest, said apparatus comprising:
   means for forming at least first and second time-varying component beams from an incident directed beam source,
   a sample fluid holding chamber having a first optical path passing therethrough, said sample chamber being positioned in the path of one of said time-varying component beams for passing said one component through said sample chamber along the sample chamber optical path passing therethrough,
   means for measuring the intensity of energy in said directed beam,
   means for varying the intensity of said directed beam in response to said directed beam measuring means, said varying means comprising
   a variable density material having a transmittance which varies along a movement axis according to a predetermined function, and
   a driver means responsive to the directed beam measuring means for positioning the material along said movement axis in the path of said directed beam for selectively attenuating said beam.

22. In a photometric analysis apparatus for analyzing, in a fluid medium, at least one sample component having a characteristic absorption wavelength of interest, said apparatus comprising:
   means for forming at least first and second time-varying component beams,
   a fluid sample chamber having an optical path passing therethrough, said chamber being positioned in the path of at least one of said beams of electromagnetic radiation, including radiation at least at said one characteristic wavelength for passing said beam through said chamber along said optical path,
   the improvement comprising
   means for measuring at respective measurement positions said first and second component beams,
   said measuring means being responsive to the sum of the DC energy in the beams and the sum of the AC energy in the combined beams, and
   means responsive to said measuring means for varying, prior to said measurement positions, the relative intensities of said first and second component beams for equalizing the AC energy in said component beams and maintaining the total DC energy substantially constant.

23. The apparatus of claim 22 wherein said measuring means further measures the difference in DC energy in the first and second beams, and
   said varying means being further responsive to said measuring means for making the DC energy in said respective beams substantially equal.

24. A method for analyzing a fluid medium having at least one sample component having a characteristic absorption wavelength of interest comprising the steps of:
   dividing an incident beam source of electromagnetic radiation, including radiation at at least the one characteristic wavelength of interest, for producing two time-varying components having a defined interdependent time varying functional relationship,
   sampling the first and second component beams for determining the relative intensities of said beams,
   altering the relative intensities of said component beams in accordance with said sampled values for providing a predetermined functional relationship between the time-varying intensities of said component beams,
   directing at least one of said component beams through said fluid medium,
   combining the component beams after said at least one beam passes through said sample fluid medium, and
   measuring the time varying components of the combined signal for determining energy absorption by said one sample fluid.

25. The method of claim 24 further comprising the steps of
   determining the intensity of said incident beam source of radiation, and
   altering the intensity of said beam to vary a beam intensity according to a predetermined function.

26. The method of claim 24 wherein said sampling step comprises the steps of
   measuring the total energy content of said component beams,
   measuring the difference in the time-varying components of said component beams, and
   measuring the difference in the DC components of said component beams.

27. The method of claim 25 wherein said altering step further comprises the step of
   altering the intensities of said component beams for maintaining a predetermined relationship between the DC intensities of said component beams.

28. In a photometric analysis apparatus for analyzing, in a fluid medium, at least one sample component having a characteristic absorption wavelength of interest, the apparatus comprising:

means for forming at least first and second time-varying component beams, a fluid sample chamber having an optical path passing therethrough, the chamber being positioned in the path of at least one of the beams of electromagnetic radiation, including radiation at least at said one characteristic wavelength for passing the beam through the chamber along the optical path, the improvement comprising means for measuring, at respective measurement positions, the first and second component beams, decision means being responsive to the relative intensities of the energy in the component beams, and means responsive to the decision means for improving the precision of a measured output of the measuring means by adjusting for differences in the AC energy in the component beams.

29. A method for analyzing a fluid medium having at least one sample component having a characteristic absorption wavelength of interest comprising the steps of:

dividing an incident beam source of electromagnetic radiation, including radiation at at least the one characteristic wavelength of interest, for producing two time-varying components having a defined interdependent time varying functional relationship, sampling the first and second component beams for determining the relative intensities of said beams, directing at least one of said component beams through said fluid medium, combining the component beams after said at least one beam passes through said sample fluid medium, measuring the time varying components of the combined signal for determining energy absorption by said one sample fluid, and altering the measurement combined signal in accordance with said sampled values according to a predetermined functional relationship.

30. A photometric analysis apparatus for analyzing a fluid medium having at least one sample component having a characteristic absorption wavelength of interest, comprising:

a beam source of electromagnetic radiation including radiation at at least said one characteristic wavelength for providing a directed beam containing said characteristic wavelength, beam modulation means in the path of said beam for providing first and second component beams, said beams having respectively time-varying portions whose intensities vary 180° out of phase at the rate of change of said beam modulation means, a sample fluid holding chamber having a first optical path passing therethrough, said sample chamber being positioned in the path of one of said component beams for passing said one component through said sample chamber along the sample chamber optical path passing therethrough, a reference fluid holding chamber having a second optical path passing therethrough, said reference fluid chamber being positioned in the path of the other of said first and second component beams for passing said other component beam through said reference chamber along the reference chamber optical path passing therethrough, means for combining said first and second component beams after passage through said sample fluid holding chamber and said reference fluid holding chamber, first means for measuring the AC component of said combined beam, second means for measuring said first and second component beams before said beams pass through said sample and reference chambers, and means responsive to said second measuring means for varying the measurement of said AC component.

* * * * *